United States Patent [19]

Karimian et al.

[11] Patent Number: 5,536,824
[45] Date of Patent: Jul. 16, 1996

[54] ORGANOSULFONYL SALTS OF 2,3'-O-CYCLOCYTIDINE

[75] Inventors: Khashayar Karimian; Bruno K. Radatus, both of Brantford, Canada

[73] Assignee: ACIC (Canada) Inc., Brantford, Canada

[21] Appl. No.: 356,498

[22] Filed: Dec. 15, 1994

Related U.S. Application Data

[62] Division of Ser. No. 930,605, Oct. 5, 1992, Pat. No. 5,399,682.

[30] Foreign Application Priority Data

Mar. 13, 1990 [CA] Canada .................................... 2012095
Mar. 13, 1990 [CA] Canada .................................... 2012096

[51] Int. Cl.[6] .......................... C07H 19/067; A61K 31/70
[52] U.S. Cl. ............................................. 536/28.5; 514/49
[58] Field of Search ............................... 536/28.5; 514/49

[56] References Cited

U.S. PATENT DOCUMENTS

| | | | |
|---|---|---|---|
| 3,792,040 | 2/1974 | Moffatt et al. | 536/28.5 |
| 3,812,098 | 5/1974 | Moffatt et al | 536/28.5 |
| 3,856,777 | 12/1974 | Ishino et al. | 536/28.5 |
| 4,118,484 | 10/1978 | Wechter et al. | 424/180 |

FOREIGN PATENT DOCUMENTS

| | | |
|---|---|---|
| 0311694 | 4/1989 | European Pat. Off. . |
| 8100177 | 8/1982 | Netherlands . |

OTHER PUBLICATIONS

Mizuno et al. Tetrahedron Letter 50:4579–4584, 1965.
Watanabe et al. J. Med. Chem. 23:1088–1094, 1980.
Wagner et al. J. Org. Chem. 39:24–30, 1974.
Fromageot et al. Tetrahedron Letters 29: 3499–3505, 1966.
Chemical Abstracts, vol. 86, p. 583, Abstract # 121712t, 1977.
Ozaki et al., Japan Kokai 76, 113, 881, Oct. 7, 1976.

*Primary Examiner*—Gary L. Kunz
*Attorney, Agent, or Firm*—Nixon & Vanderhye

[57] ABSTRACT

Compounds of Formula IV:

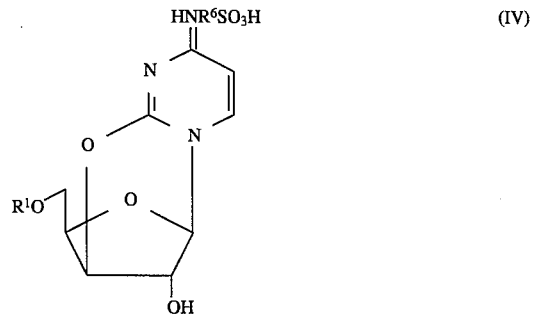

are described. In the compounds of Formula IV, $R^6$ is selected from a trifluoromethyl group, a $C_1$–$C_6$ alkyl group and a $C_6$–$C_9$ aryl group, and $R^1$ is selected from hydrogen, trityl, methoxytrityl, dimethoxytrityl, acetyl, a C2–C6 alkylacyl group, a C6–C9 arylacyl group, allyl, 2,2,2-trichloroethyl, phosphates and salts thereof, tosyl and mesyl. The above organosulfonyl salts of 2,3'-O-cyclocytidine are intermediates in the preparation of 1-(B-D-xylopentofuranose)cytosine, an inhibitor of DNA synthesis.

3 Claims, No Drawings

ORGANOSULFONYL SALTS OF 2,3'-O-CYCLOCYTIDINE

This is a Rule 60 Division of application Ser. No. 07/930,605, filed as PCT/CA91/00078, Mar. 13, 1991 now U.S. Pat. No. 5,399,682.

BACKGROUND OF THE INVENTION

1. Technical Field

The present invention relates to novel cytosine compounds, and a process for the production thereof. More specifically, the present invention relates to the production of 2,3'-O-cyclocytidine, 2,3'-O-cyclocytidine analogues and pharmaceutically acceptable salts thereof using novel 3'-O-tosylcytidine precursor compounds and pharmaceutically acceptable salts thereof. The invention also relates to the production of 1-(β-D-xylo-pentofuranosyl)cytosine, 1-(β-D-xylo-pentofuranosyl)cytosine analogues and pharmaceutically acceptable salts thereof.

2. Brief Description of the Prior Art

Mizuno et al (Tet. Lett., 4579–4584 (1965)) teach the production of 2,3'-O-cyclocytidine via a six step process which includes the production of 3'-O-mesylcytidine via a four step process from $N^4$-acetylcytidine. This corresponds to a five step process, overall, if cytidine is used as the starting material. Thus, it is not surprising that the overall yield of 3'-O-mesylcytidine produced in this manner is less than 10% (even this low yield assumes theoretical yields for two of the five steps where yield was unreported).

Fromageot et al (Tet. Lett., 3499–3505, (1966)) speculated production of $N^4$, $O^{2'}$, $O^{5'}$-triacetyl-3-O'-tosylcytidine by reacting an equilibrium mixture of $N^4$, $O^{2'}$, $O^{5'}$-isomer with a slight excess of p-toluenesulfonyl chloride in an anhydrous pyridine solution. The 3'-O-tosylcytidine derivative was assumed to be a product present in a dichloromethane phase after an arabinofuranosylcytosine derivative had been extracted from the reaction mixture with water. However, the 3'-O-tosylcytidine derivative was not isolated nor is there any disclosure or suggestion of how to prepare this derivative.

Further, as taught in Mizuno et al (Tet. Lett., 4579–4584 (1965)), 2,3'-O-cyclocytidine is produced from 3'-O-mesylcytidine as a crystalline free-base. Specifically, the last step in the process comprises reacting 3'-O-mesylcytidine with an excess of sodium t-butoxide to produce 2,3'-O-cyclocytidine. Unfortunately, the first step in the process involved conversion of $N^4$-acetylcytidine (NOTE: this was obtained from cytidine in only a 65% yield) to 2',5'-di-O-trityl-$N^4$-acetylcytidine in only a 20% yield. Accordingly, the process of Mizuno et al is deficient in that it requires an onerous number of steps to produce 2,3'-O-cyclocytidine and, when produced, 2,3'-O-cyclocytidine is obtained in a relatively low yield of less than 8.5% (even this low yield assumes theoretical yields for two of the six steps where yield was unreported). Further, Doerr et al (J. Org. Chem., 32, 1462–1471 (1967)) found it surprising that Mizuno et al reported isolating 2,3'-O-cyclocytidine in neutral form.

Fox et al (J. Am. Chem. Soc., 29, 5060–5064 (1957)) teaches the production of 1-(β-D-xylofuranosyl) cytosine via coupling of a 100% excess of protected xylosyl halide and protected mercuri-cytosine, followed by deprotection of the coupled compound to form 1-(β-D-xylo-pentofuranosyl)cytosine. Unfortunately, the coupling step provided a product in only 23% yield which corresponds to an overall yield of 1-(β-D-xylo-pentofuranosyl)cytosine of 18%. It will be appreciated that these yields would be even lower if they were based on xylose and cytosine as starting materials.

Gosselin et al (J. Med. Chem., 1986, 29, 203–213) teach the production of 1-β-D-xylofuranosyl compounds by glycosylation of purine and pyrimidine aglycons with peracylated 1-O-acetyl-α-D-xylofuranoses, followed by removal of the blocking groups.

It would be desirable to have a relatively simply process for the production of 1-(β-D-xylo-pentofuranosyl)cytosine compounds which did not comprise the use of blocking groups followed by removal of such blocking groups. It would also be desirable to have a more convenient process which provided higher or comparable yields of such 1-(β-D-xylo-pentofuranosyl)cytosine compounds.

SUMMARY OF THE INVENTION

It is an object of the present invention to provide novel 3'-O-tosylcytidine compounds.

It is another object of the present invention to provide a novel process for the production of cytidine compounds, including 3'-O-tosylcytidine compounds.

It still another object of the present invention to provide novel 2,3'-O-cyclocytidine compounds.

It is another object of the present invention to provide a novel process for the production of 2,3'-O-cyclocytidine compounds and pharmaceutically acceptable salts thereof.

It is yet another object of the present invention to provide a novel process for the production of 1-(β-D-xylo-pentofuranosyl)cytosine compounds.

Accordingly, in one of its aspects, the present invention provides a compound of Formula I, or a pharmaceutically acceptable salt thereof:

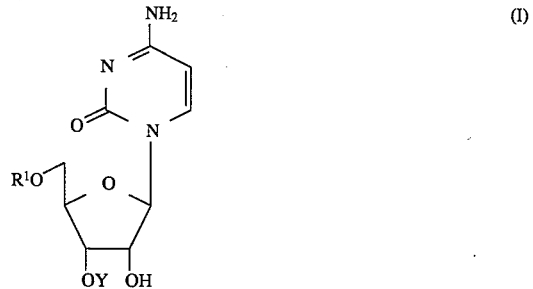

wherein Y is selected from p-toluenesulfonyl and $-SO_2CF_3$, and $R^1$ is selected from the group comprising hydrogen, trityl, methoxytrityl, dimethoxytrityl, acetyl, a $C_2$–$C_6$ alkylacyl group, a $C_6$–$C_9$ arylacyl group, allyl, 2,2,2-trichloroethyl, phosphate and salts thereof, tosyl and mesyl.

In another of its aspects, the present invention provides a process for producing a compound of Formula II, or a pharmaceutically acceptable salt thereof:

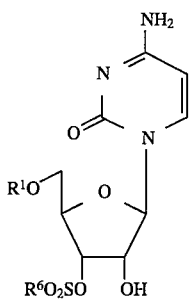

(II)

wherein $R^6$ is selected from the group comprising —$CF_3$, a $C_1$–$C_6$ alkyl group and a $C_6$–$C_9$ aryl group, which comprises the step of reacting (i) a compound of Formula III:

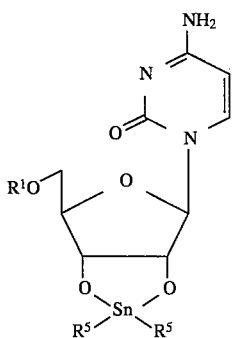

(III)

wherein $R^5$ is a $C_1$–$C_6$ alkyl group, and $R^1$ has the same meaning as above, with (ii) an amine selected from the group comprising pyridine and amines having the general formula $Q^2Q^3Q^4N$ wherein $Q^2$, $Q^3$ and $Q^4$ can be the same or different and each of $Q^2$, $Q^3$ and $Q^4$ is selected from the group comprising a $C_1$–$C_6$ alkyl group and a $C_6$–$C_9$ aryl group, in the presence of (iii) a sulfonyl compound having the general formula $R^6SO_2X$ wherein $R^6$ is selected from the group comprising —$CF_3$, a $C_1$–$C_6$ alkyl group and a $C_6$–$C_9$ aryl group, and X is selected from a halogen and $SO_3CF_3$, to produce a compound of Formula II.

In another of its aspects, the present invention provides a process for producing a compound of Formula IV:

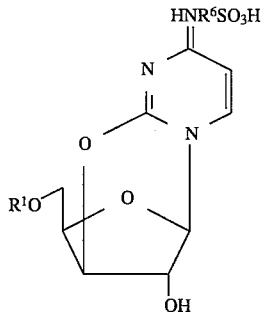

(IV)

which comprises the step of intramolecular rearrangement of a compound of Formula II:

wherein $R^1$ and $R^6$ have the same meanings as above, to produce a compound of Formula IV.

In another of its aspects, the present invention provides a process for producing a compound of Formula V:

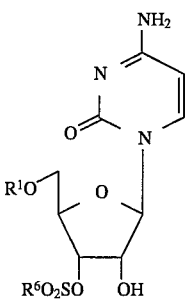

(V)

which comprises the step of intramolecular rearrangement of a compound of Formula VI:

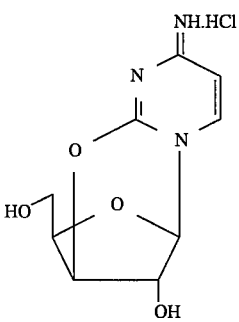

(VI)

wherein Ts is a tosyl group, followed by reaction with hydrogen chloride, to produce the compound of Formula V.

In yet another of its aspects, the present invention provides a compound of Formula IV:

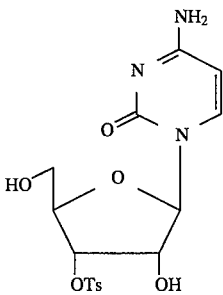

(IV)

wherein $R^6$ is selected from the group comprising a trifluoromethyl group, a $C_1$–$C_6$ alkyl group and a $C_6$–$C_9$ aryl group, and $R^1$ is selected from the group comprising hydrogen, trityl, methoxytrityl, dimethoxytrityl, acetyl, a $C_2$–$C_6$ alkylacyl group, a $C_6$–$C_9$ arylacyl group, allyl, 2,2,2-trichloroethyl, phosphates and salts thereof, tosyl and mesyl.

In still another of its aspects, the present invention provides a process for producing a compound of Formula VII, or a pharmaceutically acceptable salt thereof:

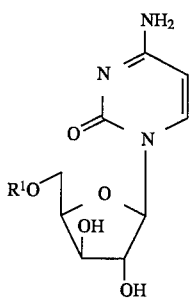
(VII)

which comprises the step of reacting (i) a compound of Formula IX, or a pharmaceutically acceptable salt thereof:

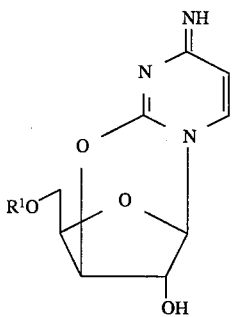
(IX)

wherein $R^1$ is selected from the group comprising hydrogen, trityl, methoxytrityl, dimethoxytrityl, acetyl, a $C_2$–$C_6$ alkylacyl group, a $C_6$–$C_9$ arylacyl group, allyl, 2,2,2-trichloroethyl, phosphates and salts thereof, tosyl and mesyl, with (ii) an amine selected from the group comprising $C_5$–$C_{12}$ heterocyclic amines and amines having the general formula:

$R^2R^3R^4N$ wherein $R^2$, $R^3$ and $R^4$ can be the same or different and are selected from the group comprising hydrogen, a $C_1$–$C_6$ alkyl group and a $C_6$–$C_9$ aryl group, with the proviso that each of $R^2$, $R^3$ and $R^4$ are not hydrogen.

In yet another of its aspects, the present invention provides a process for producing a compound of Formula VIII:

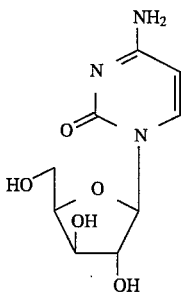
(VIII)

which comprises the step of reacting a compound of Formula V:

(V)

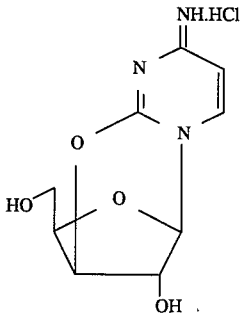

with t-butyl amine in the presence of an aqueous solvent.

In yet another of its aspects, the present invention provides a process for producing a compound of Formula VII, or a pharmaceutically acceptable salt thereof:

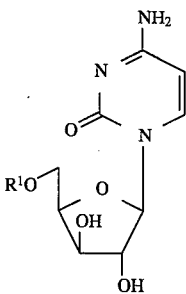
(VII)

wherein $R^1$ is selected from the group comprising hydrogen, trityl, methoxytrityl, dimethoxytrityl, acetyl, a $C_2$–$C_6$ alkylacyl group, a $C_6$–$C_9$ arylacyl group, allyl, 2,2,2-trichloroethyl, phosphates and salts thereof, tosyl and mesyl comprising the steps of:

(i) intramolecular rearrangement of a compound of Formula II:

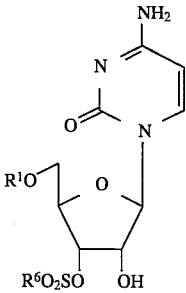
(II)

wherein $R^6$ is selected from the group comprising trifluoromethyl, a $C_1$–$C_6$ alkyl group and a $C_6$–$C_9$ aryl group, and $R^1$ is selected from the group comprising hydrogen, trityl, methoxytrityl, dimethoxytrityl, acetyl, a $C_2$–$C_6$ alkylacyl group, a $C_6$–$C_9$ arylacyl group, allyl, 2,2,2-trichloroethyl, phosphates and salts thereof, tosyl and mesyl, to produce a compound of Formula IX, or a pharmaceutically acceptable salt thereof:

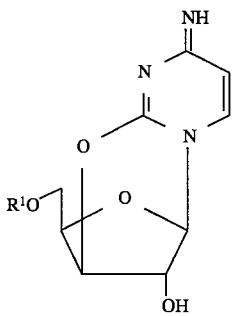

wherein $R^1$ has the above-defined meaning; and (ii) reacting the compound of Formula IX with an amine selected from the group comprising $C_5$–$C_{12}$ heterocyclic amines and amines having the general formula $$R^2R^3R^4N$$

wherein $R^2$, $R^3$ and $R^4$ can be the same or different and are selected from the group comprising hydrogen, a $C_1$–$C_6$ alkyl group and a $C_6$–$C_9$ aryl group, with the proviso that each of $R^2$, $R^3$ and $R^4$ are not hydrogen, to produce a compound of Formula VII.

DESCRIPTION OF THE PREFERRED EMBODIMENTS

Thus, in one of its aspects, the invention provides 3'-O-tosylcytidine compounds such as 3'-O-tosylcytidine (compounds of Formula I) or pharmaceutically acceptable salts thereof.

Further, compound of Formula I and compound of Formula II may be synthesized from compound of Formula III:

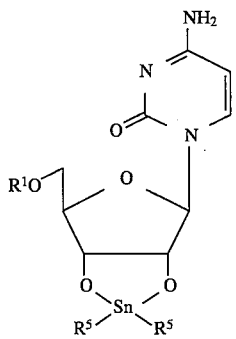

which is known. Generally, this compound may be prepared by reacting cytidine with the appropriate dialkyl-tin oxide.

In one preferred embodiment of the compound of Formula III, $R^5$ is butyl and $R^1$ is hydrogen. With these definitions for $R^5$ and $R^1$, the compound of Formula III is 2',3'-O-dibutylstannylene cytidine.

An example of a suitable "$C_2$–$C_6$ alkylacyl group" for use as $R^1$ in a compound of Formula III is acetyl. Further, an example of a suitable "$C_6$–$C_9$ arylacyl group" for use as $R^1$ benzoyl.

Provided that it does not contain a hydrogen bonded to nitrogen, the amine suitable for use in the reaction of a compound of Formula III is not particularly restricted and may be selected from the group comprising trimethylamine, triethylamine, pyridine, tripropylamine and tributylamine. The most preferred amine is triethylamine.

The reaction of the compound of Formula III with the amine is conducted in the presence of a sulfonyl compound, preferably a sulfonyl chloride compound. More preferably, the sulfonyl chloride compound is one of p-toluenesulfonyl chloride and methanesulfonyl chloride. When p-toluene sulfonyl chloride is used, the product of the process is a 3'-O-tosylcytidine compound of Formula I (i.e. Y is p-toluenesulfonyl).

Typically, the reaction of a compound of Formula III can be conducted at room temperature, preferably with agitation (such as stirring) of the reaction mixture. The reaction may be conducted in a suitable organic solvent system. Non-limiting examples of suitable organic solvents include alcohols, toluene, benzene, chloroform, dichloromethane and the like. The preferred organic solvents are alcohols, more preferably methanol.

The crude product of the above-identified reaction may be separated from the reaction mixture and purified using conventional techniques within the purview of a person skilled in the art. For example, after the reaction is complete, the solvents may be evaporated under vacuum and the resulting solid suspended and refluxed in a suitable medium (e.g. water). Thereafter, the crude product may be recrystallized from a suitable solvent, such as ethanol.

The compound of Formula II:

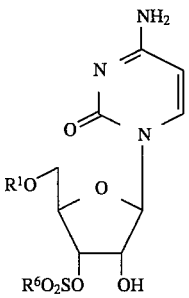

may be synthesized by reacting a 2',3'-O-dialkylstannylene cytidine compound with an organic sulfonyl compound. Preferably, the starting material is a compound of Formula VI:

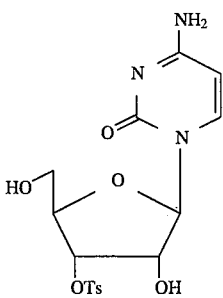

known as 3'-O-tosylcytidine, which can be suitably prepared by reaction of 2',3'-O-dialkylstannylene cytidine with tosyl chloride.

The compound of Formula II undergoes intramolecular rearrangement to produce the compound of Formula IV. Preferably, this rearrangement is conducted by refluxing the compound of Formula II in a suitable polar solvent system. Preferably, the solvent system has a boiling point of at least about 100° C. Non-limiting examples of suitable solvent systems include n-butanol, water, dimethylformamide and a mixture comprising from about 55 to about 65 percent by volume of isopropanol and from about 35 to about 45 percent by volume of toluene.

In a preferred embodiment, the compound of Formula IV can be convened to the corresponding halide salt by reaction with a hydrogen halide having the general formula $$HX$$

wherein X is a halogen. The preferred halogen is chloride thereby defining HX as hydrogen chloride. The reaction of the compound of Formula II with HX may be conducted in any suitable solvent system. Preferably, the reaction is conducted in the presence of an alcohol, more preferably ethanol.

In a preferred embodiment, 3'-O-tosylcytidine (Formula VI) undergoes intramolecular rearrangement, preferably by refluxing in an organic solvent such as n-butanol, followed by reaction with hydrogen chloride to provide the hydrochloride salt of 2,3'-O-cyclocytidine (Formula V):

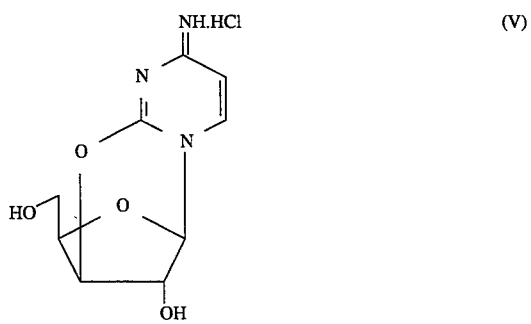

To the Applicant's knowledge, the compound of Formula V has not heretofore been known.

The crude 2,3'-O-cyclocytidine (Formula IV) may be separated from the reaction mixture using conventional techniques within the purview of a person skilled in the art. For example, after the reaction is complete, the crude 2,3'-O-cyclocytidine (Formula IV) may be converted to the corresponding halide salt by reaction with a hydrogen halide, preferably hydrogen chloride. Thereafter, the halide salt may be recrystallized from a suitable organic solvent such as an alcohol, preferably ethanol.

In the aspect of the invention involving the production of a compound of Formula VII (reaction of compound of Formula IX with an amine) described hereinbefore, the amine suitable for use is selected from the group comprising $C_5$–$C_{12}$ heterocyclic amines and amines having the general formula $$R^2R^3R^4N$$

wherein $R^2$, $R^3$ and $R^4$ can be the same or different and are selected from the group comprising hydrogen, a $C_1$–$C_6$ alkyl groups and a $C_6$–$C_9$ aryl group, with the proviso that each of $R^2$, $R^3$ and $R^4$ are not hydrogen. Thus, it will be appreciated that the use of ammonia (i.e. $R^2=R^3=R^4=H$) is outside the scope of the present invention. Non-limiting examples of suitable heterocyclic amines include pyridine and piperidine. Non-limiting examples of other amines suitable for use include t-butylamine, trimethylamine, triethylamine, tripropylamine, tributylamine, methylamine, ethylamine, diethylamine and aniline. The most preferred amine suitable for use in the present process is t-butylamine.

Preferably, the aspect of the invention involving the production of a compound of Formula VII is conducted in the presence of an aqueous solvent. Examples of suitable aqueous solvents include water and a mixture of water and at least one other solvent miscible therewith. The most preferred aqueous solvent for use in the production of a compound of Formula VII is water.

The starting material for the production of the compound of Formula VII is the compound of Formula IX described hereinbefore. The preferred form of Formula IX is as a sulfonyl salt (Formula IV). Alternatively, and most preferably, the starting material is the hydrochloride salt of 2,3'-O-cyclocytidine (Formula V):

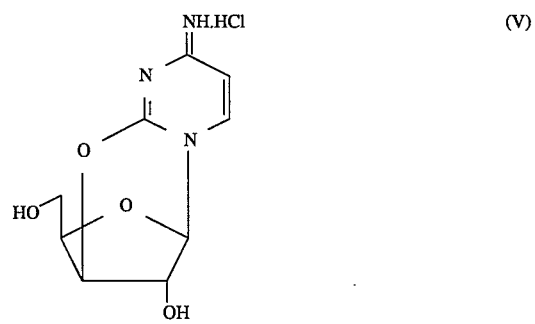

Preferably, 2,3'-O-cyclocytidine hydrochloride (Formula V) is reacted with t-butylamine in the presence of an aqueous solvent to provide 1-(β-D-xylo-pentofuranosyl)cytosine (Formula VIII):

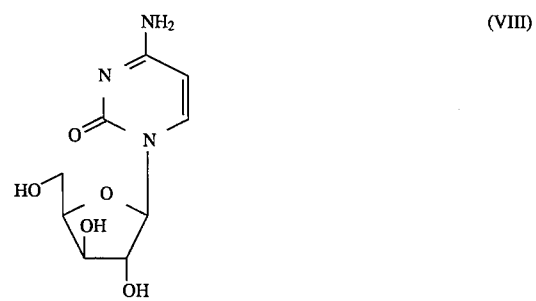

Typically, the above-noted reaction can be conducted at room temperature, preferably with agitation (such as stirring) of the reaction mixture. More preferably, the reaction is conducted in the presence of an aqueous solvent system comprising solely water.

Further, crude product may be separated from the reaction mixture and purified using conventional techniques within the purview of a person skilled in the art. For example, after the reaction is complete, the solvents may be evaporated under vacuum and the resulting solid suspended and agitated in a suitable medium to produce a purified product. Examples of such media include alcohol and mixtures containing alcohol and water. The preferred alcohol for use is ethanol.

Aspects of the invention will be described with reference to the following examples, which should not be considered to limit the scope of the invention.

EXAMPLE 1

A 500 mL flask was charged with 50 mL methanol, 1.95 g cytidine and 2 g dibutyl tin oxide. The resulting suspension was refluxed for five hours and then stirred at room temperature for 12 hours. To the mixture was then added triethylamine (7.8 mL) followed by slow addition of p-toluenesulfonyl chloride (10.68 g). The resulting mixture was stirred for 12 hours at room temperature. Thereafter, the solvents were evaporated under vacuum and chloroform (100 mL) was added to the resulting white gum. The chloroform/white gum suspension was refluxed for 15 minutes and then cooled to room temperature. The resulting white precipitate was filtered and set aside. After concentration of the filtrate under vacuum, the resulting residue was suspended in water (15 mL) at room temperature for 3 hours and then at 6° C. for 12 hours. The suspension was filtered and the solid was resuspended in 15 mL water and the mixture heated to 90° C. and then cooled to room temperature (product remained in solution). The solution was filtered through Celite and the filtrate was stirred at 6° C. for 12 hours which resulted in precipitation of a solid. The precipitate was filtered and dried under vacuum to afford 1 g of crude 3'-O-tosylcytidine tosylate salt. The crude 3'-O-tosylcytidine tosylate salt was suspended in 25 mL chloroform and stirred for one hour. The suspension was filtered and washed with 5 mL chloroform. Thereafter, the precipitate was suspended in 25 mL boiling ethanol, to which was added 1.8 mL t-butylamine (pH=8–9). The hot mixture was filtered, and the filtrate stirred at 15° C. for 16 hours. The resulting precipitate was filtered, washed with ethanol and dried to afford 0.53 g (14.9% yield) of pure 3'-O-tosylcytidine ethanol, a novel compound which had a melting point of 115°–116.5° C. (bubbles) with decomposition occurring at 160°–170°.

A sample of the novel compound was converted to the corresponding hydrochloride salt by reaction with dilute aqueous hydrochloric acid. Using a 200 MHz NMR spectrometer, an NMR spectrum of this hydrochloride salt was obtained in DMSO-d-6. The following data on peak shift, number of peaks and coupling constants was obtained from the spectrum and confirms the structure of the hydrochloride salt of 3'-tosylcytidine:

| SHIFT ($\delta$) | ASSIGNMENT |
| --- | --- |
| 2.42, s | 3H: $CH_3$ |
| 3.37, dd | 1H: $J_{4'5'} = 2.24Hz$, $J_{5'5'} = 12.44 Hz$: H-$5_1$' |
| 3.45, bs | 3H: exchangeable: $NH_3^+$ |
| 3.54, dd | 1H: $J_{4'5'} = 2.59Hz$: H-$5_2$' |
| 4.07, m | 1H: $J_{3'4'} = 3.17Hz$: H-4' |
| 4.26, t | 1H: $J_{1'2'} = 6.04Hz$, $J_{2'3'} = 4.93 Hz$: H-2' |
| 4.85, dd | 1H: H-3' |
| 5.76, d | 1H: H-1' |
| 6.19, d | 1H: $J_{56} = 7.80Hz$: H-5 |
| 7.48, d | 2H: $J_{Tosy123} = 8.40$: Tosyl H-3 |
| 7.84, d | 2H: Tosyl H-2 |
| 8.13, d | 1H: H-6 |
| 8.75 9.85, 2 × s | 2 × 1H, exchangeable: C2'-OH and C5'OH |

EXAMPLE 2

3'-O-Tosylcytidine ethanol (17.72 g; 0.04 moles) was suspended in 100 mL n-butanol and thereafter reluxed for 3 hours. The reaction mixture was evaporated to a thin syrup weighing 34 g and ethanol (30 mL), to which had been added 6 g of acetyl chloride, was added to the syrup and mixed therewith. The mixture was seeded and scratched to yield a precipitate, and allowed to stand at −20° C. for 1.5 hours. The precipitate was filtered and washed with ethanol to afford 8.35 g of off-white crystals which had a melting point of 191°–193° C. (decomposed). The filtrate and washings were concentrated to a thin syrup. The thin syrup was dissolved in water (150 mL) and 6 mL of 32% aqueous hydrochloric acid was then added. The aqueous solution was extracted with ethyl acetate in a continuous extractor for 18 hours. Thereafter, the aqueous phase was evaporated to about 1.8 g and recrystallized from ethanol to yield 0.59 g of off-white crystals which were combined with the 8.35 g of crystals described above. The combined batch of off-white crystals (8.94 g) was recrystallized from aqueous ethanol to afford 8.11 g (77% yield) of pure 2,3'-O-cyclocytidine hydrochloride as white crystals having a melting point of 196.5°–199.0° C. (decomposed). Using a 200 MHz NMR spectrometer, an NMR spectrum of this 2,3'-O-cyclocytidine hydrochloride was obtained in DMSO-d-6. The following data on peak shift, number of peaks and coupling constants was obtained from the spectrum and confirms the structure of the product:

| SHIFT ($\delta$) | ASSIGNMENT |
| --- | --- |
| 3.62, ABm | 2H: $J_{4,5_1} = J_{4,5_2} = 5.6Hz$: H-$5_1$' and H-$5_2$' |
| 4.47, td | 1H: $J_{3,4} = 3.6Hz$: H-4' |
| 4.88, bs | 1H: H-2' |
| 5.12, t | 1H: $J_{5'1,OH} = J_{5'1,OH} = 5.2Hz$, exchangeable: C5'-OH |
| 5.16, m | 1H: H-3' |
| 5.90, s | 1H: H-1' |
| 6.50, d | 1H: $J_{56} = 7.3Hz$: H-5 |
| 6.70, bs | 1H: exchangeable: C2-OH |
| 8.18, d | 1H: H-6 |
| 9.13, bs | 2H: exchangeable: $NH_2^+$ |

EXAMPLE 3

2,3'-O-Cyclocytidine hydrochloride (5.0 g) was dissolved in 50 mL water. t-Butylamine (2.9 g) was added, with stirring, to the 2,3'-O-cyclocytidine hydrochloride solution. After 1.5 hours, the solvent was evaporated and 25 mL ethanol was added to the resulting oil. The oil was dissolved in the ethanol with gentle heating which subsequently resulted in the spontaneous formation of a mass of crystalline material. The crystalline material was kept at −20° C. for 2 hours and thereafter was filtered, washed with 5 mL ethanol and dried to afford 4.02 g (86.5% yeild) pure 1-($\beta$-D-xylo-pentofuranosyl)cytosine (Formula VI). The product had a melting point of 239.0°–240.5° C. which is in general agreement with the values reported by Fox et al and Gosselin et al described hereinabove. Using a 200 MHz NMR spectrometer, an NMR spectrum of 1-($\beta$-D-xylo-pentofuranosyl)cytosine was obtained in DMSO-d-6. The following data on peak shift, number of peaks and coupling constants was obtained from the spectrum and confirms the structure of the product:

| SHIFT ($\delta$) | ASSIGNMENT |
| --- | --- |
| 3.68, ABm | 2H: $J_{5,OH} = J_{5,OH} = 5.6Hz$: H-$1^5$ and H-$5_2$' |
| 3.87, ABm | 2H: H-2' and H-3' |
| 4.07, m | 1H: H-4' |
| 4.74, t | 1H: exchangeable: C5'-OH |
| 5.30, d | 1H: $J_{2,OH} = 3.66Hz$, exchangeable: C2'-OH |
| 5.62, s | 1H: H-1' |
| 5.67, d | 1H: $J_{3',OH} = 4.76Hz$, exchangeable: C3'-OH |
| 5.68, d | 1H: $J_{56} = 7.47Hz$: H-5 |
| 7.09, bd | 2H: $NH_2$ |
| 7.69, d | 1H: H-6 |

What is claimed is:

1. A compound of Formula IV:

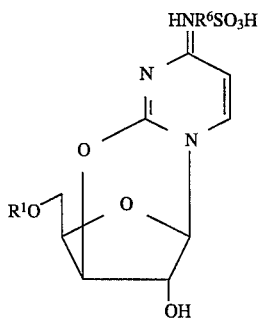

(IV)

wherein $R^6$ is selected from the group consisting of a trifluoromethyl group, a $C_1$–$C_6$ alkyl group and a $C_6$–$C_9$ aryl group, and $R^1$ is selected from the group consisting of hydrogen, trityl, methoxytrityl, dimethoxytrityl, acetyl, a $C_2$–$C_6$ alkylacyl group, a $C_6$–$C_9$ arylacyl group, allyl, 2,2,2-trichloroethyl, phosphates and salts thereof, tosyl and mesyl.

2. The compound defined in claim 1, wherein $R^1$ is hydrogen.

3. The compound defined in claim 1, wherein $R^6$ is 4-methylphenyl.

* * * * *